US009420943B2

(12) United States Patent  
Kawase

(10) Patent No.: US 9,420,943 B2  
(45) Date of Patent: Aug. 23, 2016

(54) ENDOSCOPE REPROCESSING APPARATUS

(71) Applicant: OLYMPUS CORPORATION, Tokyo (JP)

(72) Inventor: Takahiko Kawase, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/802,444

(22) Filed: Jul. 17, 2015

(65) Prior Publication Data

US 2015/0320303 A1  Nov. 12, 2015

Related U.S. Application Data

(63) Continuation of application No. PCT/JP2014/076806, filed on Oct. 7, 2014.

(30) Foreign Application Priority Data

Nov. 8, 2013  (JP) ................................. 2013-232064

(51) Int. Cl.
*A61B 1/12*   (2006.01)
*A61L 2/24*   (2006.01)
*A61B 1/00*   (2006.01)

(52) U.S. Cl.
CPC ............. *A61B 1/125* (2013.01); *A61B 1/00057* (2013.01); *A61B 1/123* (2013.01); *A61L 2/24* (2013.01); *A61B 1/00006* (2013.01)

(58) Field of Classification Search
CPC ....... A61B 1/12; A61B 1/125; A61B 1/00057
See application file for complete search history.

(56) References Cited

U.S. PATENT DOCUMENTS

2007/0048183 A1* 3/2007 Nguyen ................. A61B 1/123
422/62

FOREIGN PATENT DOCUMENTS

| JP | H07-324365 A | 12/1995 |
| JP | 2002-034915 A | 2/2002 |
| JP | 2003-010115 A | 1/2003 |
| JP | 2006-230709 A | 9/2006 |
| JP | 2007-125385 A | 5/2007 |

OTHER PUBLICATIONS

International Search Report dated Dec. 22, 2014 issued in PCT/JP2014/076806.

* cited by examiner

*Primary Examiner* — Sean E Conley
(74) *Attorney, Agent, or Firm* — Scully, Scott, Murphy & Presser, P.C.

(57) ABSTRACT

An endoscope reprocessing apparatus has a calculation section and a control section. The calculation section determines whether a flow rate or pressure information is in a region in which the circulation conduit is determined to be clogged, of a region exceeding a predetermined threshold value and a region below the predetermined threshold value, and determines whether newest flow rate or pressure information has a correlation with a change-over-time prediction axis when the flow rate or pressure information is in the region in which the circulation conduit is determined to be clogged. The control section performs a first measure relating to removal of scale when it is determined that the flow rate or pressure information has a correlation with the change-over-time prediction axis, and performs a second measure different from removal of scale when it is determined that the flow rate or pressure information does not have the correlation.

7 Claims, 9 Drawing Sheets

| WEIGHT [g] OF CITRIC ACID DISSOLVED IN 100 ml OF WATER | MASS PERCENT CONCENTRATION [%] OF CITRIC ACID AQUEOUS SOLUTION | COMPONENT OF SCALE | |
|---|---|---|---|
| | | CALCIUM CARBONATE | CALCIUM PHOSPHATE |
| 1 | 0.99 | × | × |
| 5 | 4.76 | △ | × |
| 10 | 9.09 | ○ | ○ |
| 20 | 16.7 | ○ | ○ |
| 30 | 23.1 | ○ | ○ |
| 40 | 28.6 | ○ | ○ |
| 50 | 33.3 | ○ | △ |

○: COMPLETELY DISSOLVED
△: PARTIALLY REMAINING
×: NOT DISSOLVED

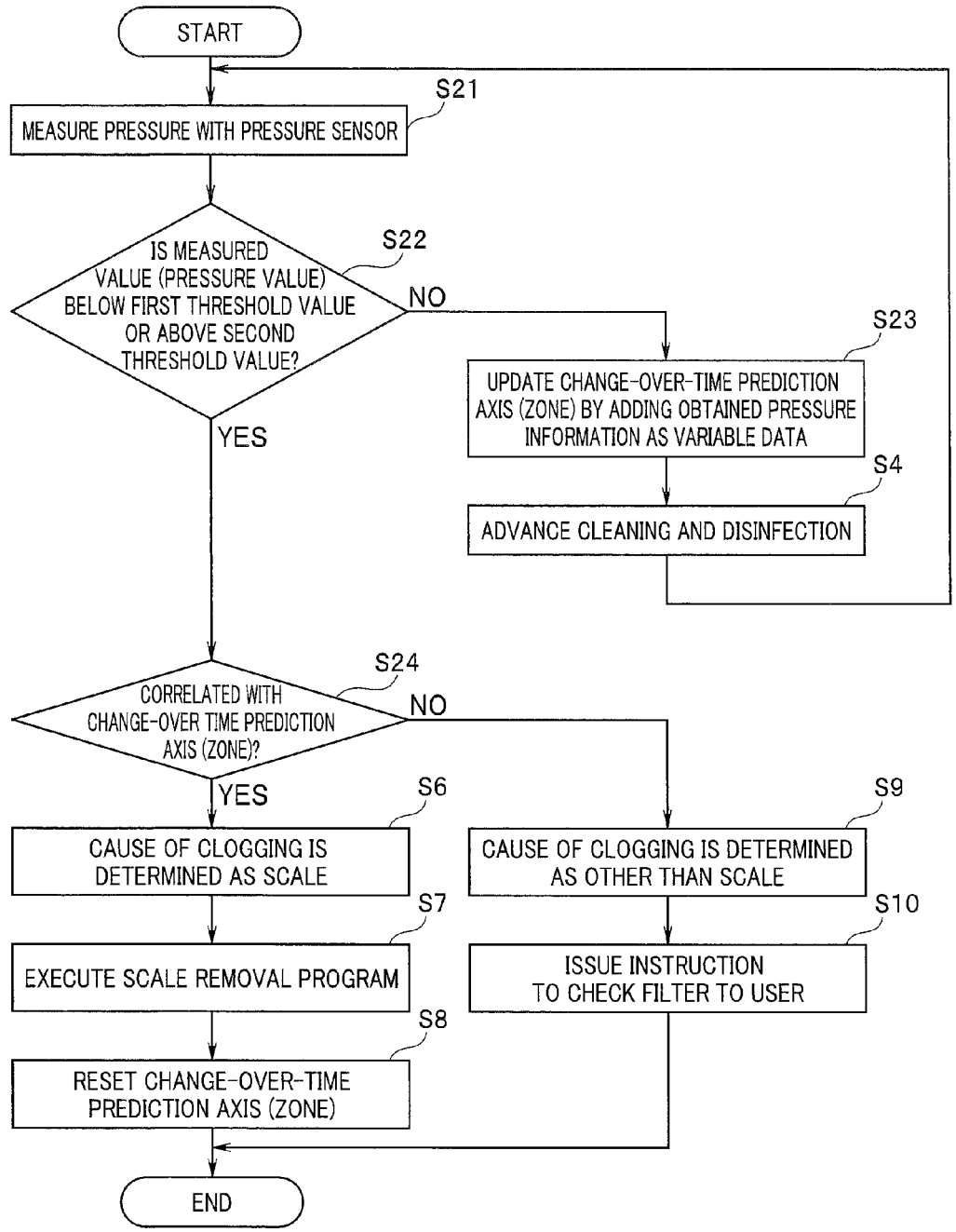

ENDOSCOPE REPROCESSING APPARATUS

CROSS REFERENCE TO RELATED APPLICATION

This application is a continuation application of PCT/JP20141076806 filed on Oct. 7, 2014 and claims benefit of Japanese Application. No. 2013-232064 filed in Japan on Nov. 8, 2013, the entire contents of which are incorporated herein by this reference.

BACKGROUND OF THE INVENTION

1. Field of the Invention

The present invention relates to an endoscope reprocessing apparatus that identifies a cause of clogging in an apparatus internal conduit.

2. Description of the Related Art

Conventionally, a configuration of an endoscope reprocessing apparatus has been well-known, which cleans and disinfects an inside of an endoscope conduit by the endoscope conduit being connected to an endoscope connecting portion of the endoscope reprocessing apparatus, and a liquid being supplied into the endoscope conduit from a liquid supply source via a liquid supply conduit, a circulation conduit and the endoscope connecting portion in the endoscope reprocessing apparatus.

In the endoscope reprocessing apparatus, in the circulation conduit, a pump that circulates a liquid is provided, and a pressure sensor and a flow rate sensor that measure the pressure and the flow rate of the liquid which passes through the circulation conduit are provided. The endoscope reprocessing apparatus detects clogging in the endoscope conduit and clogging in the circulation conduit by monitoring the pressure and the flow rate which are measured by the pressure sensor and the flow rate sensor.

For example, Japanese Patent Application Laid-Open Publication No. 2007-125385 discloses an endoscope reprocessing apparatus which is provided with pressure sensors in a respective plurality of apparatus internal conduits, and detects excessive pressures of the respective apparatus internal conduits by the pressure sensors to detect the apparatus internal conduit where clogging has occurred.

As clogging in the apparatus internal conduits like this, there exist sudden clogging due to entry of contaminants or the like into the apparatus internal conduits, clogging due to scale that accumulates in the apparatus internal conduits over a long time period, and the like. Scale is calcium carbonate or the like precipitated on an apparatus internal conduit, when water with a high hardness dries in the apparatus internal conduit.

SUMMARY OF THE INVENTION

An endoscope reprocessing apparatus of one aspect of the present invention has a fluid supply conduit that supplies a fluid to at least one of a channel or an outer sheath of an endoscope, a measurement section that measures a flow rate or a pressure of the fluid that flows through the fluid supply conduit, an information accumulating section that accumulates the flow rate or the pressure which is measured by the measurement section as flow rate or pressure information associated with a measurement timing, a prediction section that calculates a change-over-time prediction axis of the flow rate or the pressure from the flow rate or pressure information which is accumulated, when a predetermined number or more of pieces of the flow rate or pressure information are accumulated in the information accumulating section, a threshold value determining section that determines whether the flow rate or pressure information which is measured by the measurement section is in a region in which the fluid supply conduit is determined to be clogged, of a region exceeding a predetermined threshold value and a region below the predetermined threshold value, a correlation determining section that determines whether or not newest flow rate or pressure information that is measured by the measurement section has a correlation with the change-over-time prediction axis, when the threshold value determining section determines that the flow rate or pressure information is in the region in which the fluid supply conduit is determined to be clogged, and a control section that performs a first measure relating to removal of scale when the correlation determining section determines that the newest flow rate or pressure information has the correlation, and performs a second measure different from removal of scale when the correlation determining section determines that the newest flow rate or pressure information does not have the correlation.

BRIEF DESCRIPTION OF THE DRAWINGS

FIG. 9A is a diagram for explaining detection of scale by a system control unit 41a;

FIG. 9B is a diagram for explaining the detection of scale by the system control unit 41a; and FIG. 10 is a flowchart for explaining scale detection processes of an endoscope reprocessing apparatus 1a according to the second embodiment.

DETAILED DESCRIPTION OF THE PREFERRED EMBODIMENTS

Hereinafter, embodiments of the present invention will be described with reference to the drawings.

First Embodiment

Figure 1:
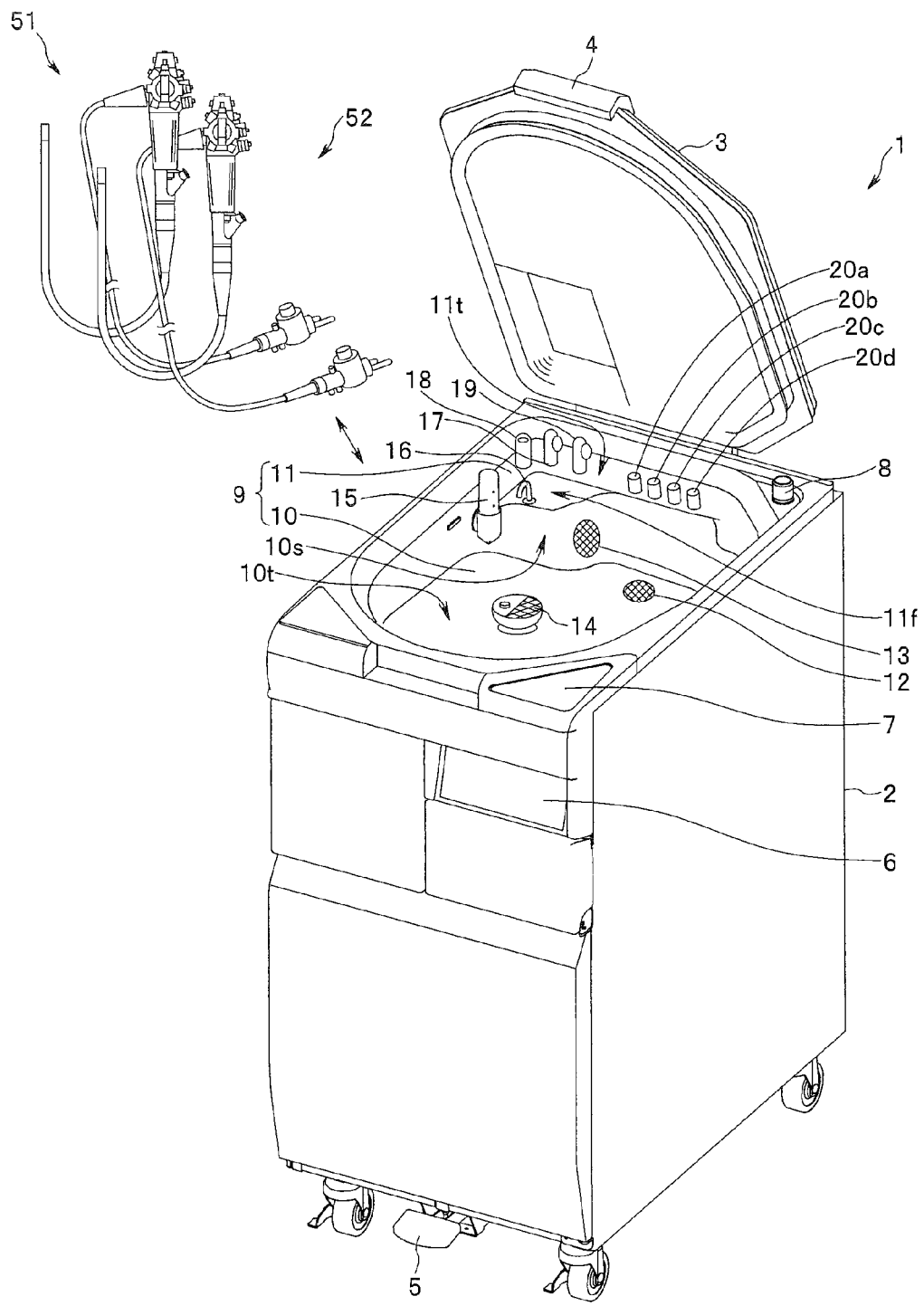
FIG. 1 is a perspective view showing one example of an endoscope reprocessing apparatus according to a first embodiment.

First, with use of FIG. 1, a configuration of an endoscope reprocessing apparatus of a first embodiment will be described. FIG. 1 is a perspective view showing one example of the endoscope reprocessing apparatus according to the first embodiment.

As shown in FIG. 1, an endoscope reprocessing apparatus 1 is an apparatus that simultaneously cleans and disinfects two endoscopes 51 and 52, and is configured by an apparatus main body 2, and a top cover 3 that is a lid portion connected to an upper portion of the apparatus main body 2 to be openable and closable via a hinge not illustrated, for example. Note that although the endoscope reprocessing apparatus 1 is configured to clean and disinfect the two endoscopes 51 and 52, the number of endoscopes that can be cleaned and disinfected in the endoscope reprocessing apparatus 1 is not limited to two, and may be one, or three or more.

In a state in which the top cover 3 is closed on the apparatus main body 2, the apparatus main body 2 and the top cover 3 are configured to be locked after being closed, by, for example, a latch 4 that is placed at positions facing each other in the apparatus main body 2 and the top cover 3.

Further, a pedal switch 5 for opening the top cover 3 which is closed on the upper portion of the apparatus main body 2, upward of the apparatus main body 2 by a pressing operation of an operator, is placed at a lower portion of a front surface in the drawing of the apparatus main body 2.

Further, a sub operation panel 6 on which instruction switches for performing display of a cleaning and disinfecting time period and various operation instructions are placed is provided on, for example, an upper portion at a right half, which is on the front surface of the apparatus main body 2.

Further, a main operation panel 7 on which a cleaning and disinfecting operation start switch of the apparatus main body 2, a scale removal program execution switch for executing a scale removal program which is executed when scale is to be removed and the like are placed is provided near a right end in the drawing at the front surface side which an operator approaches, for example, on a top surface of the apparatus main body 2.

Further, a water supply hose connection port 8 to which a water supply hose which is connected to a tap water faucet and is for supplying tap water to the apparatus main body 2 is connected is placed at a back surface side that faces the front surface which the operator approaches and is on the top surface of the apparatus main body 2. Note that in the water supply hose connection port 8, a mesh filter that filters tap water may be placed.

Further, a cleaning and disinfecting tank 9 in which an endoscope accommodation port that opens upward is opened and closed by the top cover 3, and the endoscopes 51 and 52 can be accommodated is provided in a substantially central portion on the top surface of the apparatus main body 2. The cleaning and disinfecting tank 9 is configured by a tank main body 10, and a terrace portion 11 that is continuously provided peripherally at an outer peripheral edge of the endoscope accommodation port of the tank main body 10.

The tank main body 10 can accommodate the endoscopes 51 and 52 when the endoscopes 51 and 52 after use are cleaned and disinfected, and an exhaust port 12 for draining a cleaning solution, water, a disinfecting solution, a citric acid aqueous solution and the like, which are fluids that are supplied to the tank main body 10, from the tank main body 10 is provided on a bottom surface 10t that is a surface in a tank of the tank main body 10.

Further, a circulation port 13 for supplying fluids that are the cleaning solution, the water, the disinfecting solution, the citric acid aqueous solution and the like again to the tank main body 10 from a circulation nozzle 18 is provided in an arbitrary position on a peripheral side surface 10s that is a surface in the tank of the tank main body 10. Further, the circulation port 13 supplies the cleaning solution, the water and the disinfecting solution which are supplied to the tank main body 10 to respective conduits that are placed inside the endoscopes 51 and 52 from the tank main body 10. Note that the circulation port 13 may be provided on the bottom surface 10t of the tank main body 10.

Further, a cleaning case 14 for accommodating buttons of respective scope switches and the like, forceps plugs and the like of the endoscopes 51 and 52, and cleaning and disinfecting the buttons, the forceps plugs and the like together with the endoscopes 51 and 52 is placed substantially in a center of the bottom surface 10t of the tank main body 10.

Further, a water level sensor 15 with a cover, for detecting water levels of the liquids such as the cleaning solution, the water, the disinfecting solution and the citric acid aqueous solution which are supplied to the tank main body 10 and reliably supplying the liquids to set water levels in the cleaning and disinfecting tank 9 is provided at an arbitrary position on the side surface 10s of the tank main body 10.

The terrace portion 11 of the cleaning and disinfecting tank 9 is formed by having an inclined surface pointing diagonally upward, more specifically, a peripheral terrace surface 11t that is inclined at a specified angle with respect to the bottom surface 10t, for example, of the tank main body 10.

A cleaning agent nozzle 16 for supplying the cleaning solution to the tank main body 10 from a cleaning agent tank not illustrated is placed on a surface other than the terrace surface 11t of the terrace portion 11, that is, a surface 11f that is parallel with the bottom surface 10t of the tank main body 10. Note that the cleaning agent nozzle 16 may be placed on the terrace surface 11t.

Further, a disinfecting solution nozzle 17 for supplying the disinfecting solution to the tank main body 10 from a disinfecting solution tank 33 is placed on the terrace surface 11t of the terrace portion 11.

Further, the circulation nozzle 18 for supplying water for use in cleaning or rinsing to the tank main body 10, or supplying the cleaning solution, the water, the disinfecting solution, the citric acid aqueous solution or the like which is sucked from the circulation port 13 of the tank main body 10 to the tank main body 10 again is placed on the terrace surface 11t.

Further, a pump valve nozzle 19 that will be described later is placed on the terrace surface 11t. Note that the disinfecting solution nozzle 17, the circulation nozzle 18 and the pump valve nozzle 19 may be placed on the parallel surface 11f.

Further, endoscope connecting portions 20a and 20d that are connected to conduits of the endoscope 51 via tubes are provided at predetermined positions fronting onto the cleaning and disinfecting tank 9 of the apparatus main body 2. Note that the number of the endoscope connecting portions which are connected to the conduits of the endoscope 51 is not limited to two.

Likewise, endoscope connecting portions 20c and 20d that are connected to conduits of the endoscope 52 via tubes are provided at predetermined positions fronting onto the cleaning and disinfecting tank 9 of the apparatus main body 2. Note that the number of the endoscope connecting portions which are connected to the conduits of the endoscope 52 is not limited to two, either.

Figure 2:
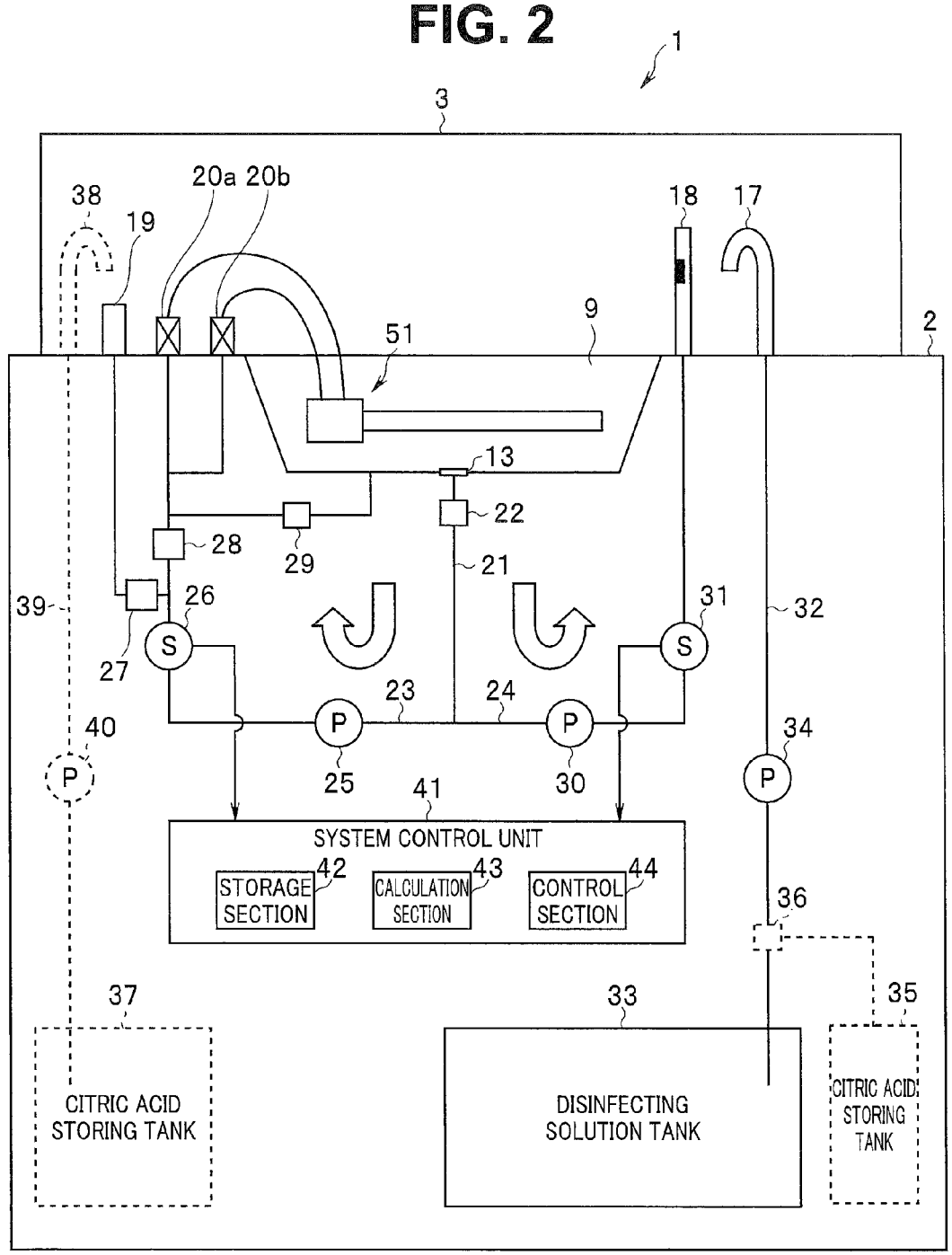
FIG. 2 is a block diagram for explaining an internal configuration of the endoscope reprocessing apparatus according to the first embodiment.

Next, an internal configuration of the endoscope reprocessing apparatus 1 will be described. FIG. 2 is a block diagram for explaining the internal configuration of an endoscope reprocessing apparatus according to a first embodiment. Note that FIG. 2 shows an example in which the endoscope 51 is connected via the endoscope connecting portions 20a and 20b, but the endoscope 52 may be connected via the endoscope connecting portions 20c and 20d which are not illustrated.

The circulation port 13 of the tank main body 10 is connected to one end of a circulation conduit 21. A filter 22 that removes contaminants and the like to be a cause of clogging is provided at a predetermined position of the circulation conduit 21. Further, the other end of the circulation conduit 21 branches into two so as to communicate with one end of a circulation conduit 23 and one end of a circulation conduit 24.

The other end of the circulation conduit 23 communicates with the cleaning and disinfecting tank 9, the pump valve nozzle 19, and the endoscope connecting portions 20a and 20b. In the circulation conduit 23, a pump 25, a flow rate sensor 26, a pump valve 27, an electromagnetic valve 28 and a relief valve 29 are provided in sequence from one end side midway of the conduit.

Further, the other end of the circulation conduit 24 communicates with the circulation nozzle 18. In the circulation conduit 24, a pump 30 and a flow rate sensor 31 are provided in sequence from one end side midway of the conduit. In the present embodiment, the circulation conduits 21 and 23 configure a fluid supply conduit that supplies fluids to channels of the endoscopes 51 and 52, and the circulation conduits 21 and 24 configure a fluid supply conduit that supplies fluids to outer sheaths of the endoscopes 51 and 52.

The flow rate sensors 26 and 31 as flow rate measuring sections respectively measure flow rates of fluids that pass through the circulation conduits 23 and 24, and are configured by electromagnetic induction type flow meters, for example. Measured values (flow rate values) that are measured by the flow rate sensors 26 and 31 are outputted to a system control unit 41.

The pump valve 27 and the electromagnetic valve 28 are controlled to open and close by the system control unit 41. When the pump valve 27 is closed and the electromagnetic valve 28 is opened by the system control unit 41, the fluids in the cleaning and disinfecting tank 9 are supplied to the respective conduits of the endoscope 51 via the circulation port 13, the circulation conduit 21, the circulation conduit 23 and the endoscope connecting portions 20a and 20b by driving of the pump 25.

Further, when the pump valve 27 is opened and the electromagnetic valve 28 is closed by the system control unit 41, the fluids in the cleaning and disinfecting tank 9 are supplied to the cleaning and disinfecting tank 9 again via the circulation port 13, the circulation conduit 21, the circulation conduit 23 and the pump valve nozzle 19 by driving of the pump 25. Thereby, a flow rate of the pump 25 as a single body can be measured by the flow rate sensor 26.

Further, the fluids in the cleaning and disinfecting tank 9 are supplied to the cleaning and disinfecting tank 9 again via the circulation port 13, the circulation conduit 21, the circulation conduit 24 and the circulation nozzle 18 by driving of the pump 30.

The disinfecting solution nozzle 17 is connected to one end of the disinfecting solution conduit 32, and the other end of the disinfecting solution conduit 32 communicates with a disinfecting solution tank 33. A pump 34 is provided midway of the disinfecting solution conduit 32, and the disinfecting solution stored in the disinfecting solution tank 33 is supplied into the cleaning and disinfecting tank 9 via the disinfecting solution conduit 32 and the disinfecting solution nozzle 17 by driving of the pump 34.

Note that though details will be described later, the citric acid aqueous solution is charged into the disinfecting solution tank 33 after the disinfecting solution stored in the disinfecting solution tank 33 is discharged, and an inside of the disinfecting solution tank 33 is rinsed with water, but a citric acid storing tank 35 or 37 as a removal chemical storing section in which the citric acid aqueous solution is stored may be provided separately from the disinfecting solution tank 33.

When the citric acid storing tank 35 is provided in the apparatus main body 2, a three-way electromagnetic valve 36 is provide midway of the disinfecting solution conduit 32. The three-way electromagnetic valve 36 is a valve that switches communication of the disinfecting solution nozzle 17 and the disinfecting solution tank 33, or communication of the disinfecting solution nozzle 17 and the citric acid storing tank 35 by internal valves. That is to say, the disinfecting solution nozzle 17 communicates with either the disinfecting solution tank 33 or the citric acid storing tank 35 in response to a switching operation of the three-way electromagnetic valve 36.

When the citric acid storing tank 37 is provided in the apparatus main body 2, a conduit 39 with one end communicating with the citric acid storing tank 37 and the other end communicating with the nozzle 38 is provided, and a pump 40 is provided midway of the conduit 39.

The system control unit 41 is configured by a storage section 42, a calculation section 43, and a control section 44. The system control unit 41 performs control of the entire system, and performs detection of scales that precipitate on the circulation conduits 21, 23, 24 and the like based on the measured values from the flow rate sensors 26 and 31.

Note that the present embodiment is configured to be provided with the flow rate sensors 26 and 31 as the flow rate sensors for detection of scales, but may be configured to be provided with either one of the flow rate sensors 26 and 31.

One cause of precipitation of scale is that water containing hardness components is dried in a conduit, and therefore, scale is highly likely to precipitate on an atmosphere open conduit in which water in the conduit is easily dried. In the present embodiment, scale is highly likely to precipitate on the circulation conduit 24 which is not closed with a valve or the like from the cleaning and disinfecting tank 9. Therefore, the configuration may be such that the flow rate sensor 31 is provided only in the circulation conduit 24 which is an atmosphere open conduit.

However, the circulation conduit 23 in FIG. 2 can be also made an atmosphere open conduit by being opened with connectors or the like being connected to the endoscope connecting portions 20a and 20b. Further, even in a state in which the endoscope 51 is connected to the endoscope connecting portions 20a and 20b, the pump valve 27 is opened, and the electromagnetic valve 28 is closed, whereby the circulation conduit 23 can be made an atmosphere open conduit. Therefore, the flow rate sensor 26 of the circulation conduit 23 can be also used as the flow rate sensor for scale detection.

Figures 3, 4:
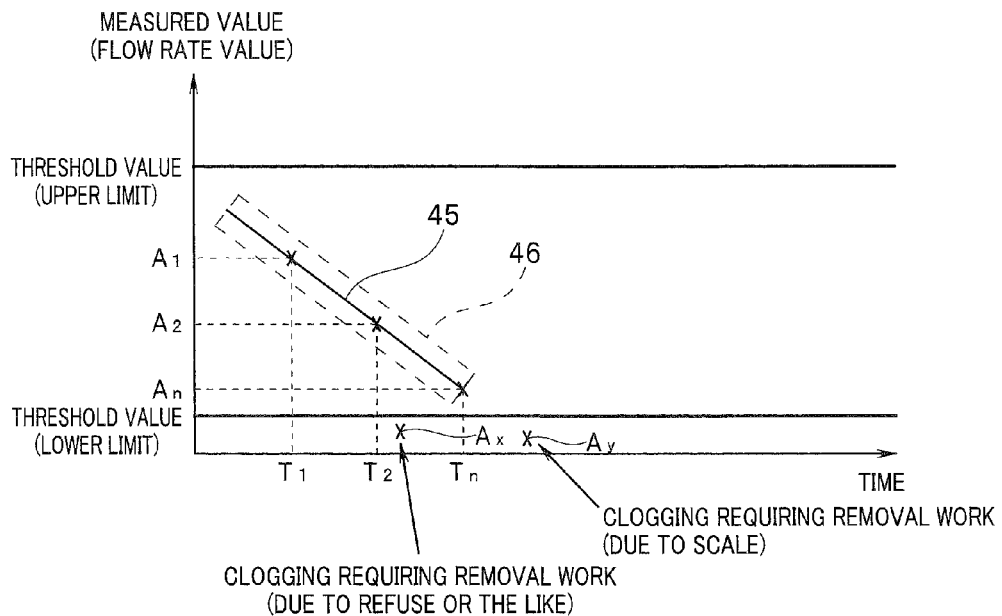
FIG. 3 is a diagram for explaining detection of scale by a system control unit 41.
FIG. 4 is a diagram for explaining a relation between a concentration of a citric acid aqueous solution and a scale removal result.

Here, detection of scale by the system control unit 41 will be described with use of FIG. 3. FIG. 3 is a diagram for explaining detection of scale by the system control unit 41. Note that in the following explanation, detection of scale according to the measured value from the flow rate sensor 31 will be described, but detection of scale can be similarly performed with the flow rate sensor 26.

When cleaning and disinfecting of the endoscopes 51 and 52 are carried out, the flow rate sensor 31 measures a flow rate of the fluid which passes in the circulation conduit 24, and outputs the measured value to the system control unit 41. The calculation section 43 of the system control unit 41 determines whether or not the measured value from the flow rate sensor 31 deviates from a threshold value. Like this, the calculation section 43 configures a threshold value determining section that determines whether or not flow rate information which is measured by the flow rate sensor 31 deviates from a predetermined threshold value. More specifically, the calculation section 43 determines whether or not the measured value from the flow rate sensor 31 is below a threshold value (a lower limit). Note that in the following explanation, the threshold value (the lower limit) is also called a first threshold value, and a threshold value (an upper limit) is also called a second threshold value.

The calculation section 43 determines that the circulation conduits 21 and 24 do not have clogging when the measured value from the flow rate sensor 31 exceeds the first threshold value, and stores a measured value A in the storage section 42 together with a measurement timing T at a time thereof. The aforementioned measurement timing T can be information from which a sequential relation in a temporal axis of the respective measured values A in a plurality of measured values A is understandable. For example, the measurement timing T may be a date, may be an elapsed time period from first flow rate measurement, may be an elapsed time period from a predetermined date, or may be simply a measured sequence (first, second, . . . ). For example, in the storage section 42, the measured value A1 and a time point T1 at a time thereof, a measured value A2 and a time point T2 at a time of thereof, . . . , and a measured value An and a time point Tn at a time thereof are stored. Note that for the measured value A, an average value that is obtained by measured values, which are measured a plurality of times in a short time period, being averaged may be used. Like this, the storage section 42 configures a flow rate information accumulating section that accumulates flow rates measured by the flow rate sensor 31 as flow rate information associated with the measurement timing T.

The calculation section 43 calculates a change-over-time prediction axis 45 from a relation between the measured values A and the time points T which are stored in the storage section 42. Like this, the calculation section 43 configures a prediction section that calculates the change-over-time prediction axis 45 of the flow rate from the accumulated flow rate information when a predetermined number or more of pieces of flow rate information are accumulated in the storage section 42. Note that in the example in FIG. 3, the change-over-time prediction axis 45 is a straight line (the measured value A and the time point T are in a proportional relation), but is not limited to this. Further, the calculation section 43 may calculate a change-over-time prediction zone 46 with a margin given to the change-over-time prediction axis 45.

The calculation section 43 calculates the change-over-time prediction axis 45 by obtaining a straight line that passes an intersection of the measured value A1 and the time point T1 and an intersection of the measured value A2 and the time point T2, and calculates the change-over-time prediction axis 45 by obtaining a regression line from the measured value A1 and the time point T1 to a measured value An−1 and a time point Tn−1, for example.

The calculation section 43 determines that the circulation conduits 21 and 24 have clogging when the measured value A from the flow rate sensor 31 is below the first threshold value. Subsequently, the calculation section 43 determines whether or not there is a correlation between the measured value A and the change-over-time prediction axis 45, more specifically, determines whether or not the measured value A is on the change-over-time prediction axis 45. Note that the calculation section 43 may determine whether or not the measured value A is within the change-over-time prediction zone 46. Like this, the calculation section 43 configures a correlation determining section that determines whether or not newest measured flow rate information has a correlation with the change-over-time prediction axis 45 when the calculation section 43 determines that the flow rate information from the flow rate sensor 31 deviates from the threshold value.

When it is determined that there is no correlation between the measured value A and the change-over-time prediction axis 45 by the calculation section 43, the control section 44 determines that clogging is due to something other than scale, for example, due to a contaminant or the like, and instructs a second measure different from removal of scale, in this case, instructs a user to check the filter 22. For example, a measured value Ax in FIG. 3 is not on the change-over-time prediction axis 45 (or, the measured value Ax is not within the change-over-time prediction zone 46), and therefore, the calculation section 43 determines that there is no correlation between the measured value Ax and the change-over-time prediction axis 45 (or the change-over-time prediction zone 46).

As above, when it is determined that there is no correlation between the measured value Ax and the change-over-time prediction axis 45 (or the change-over-time prediction zone 46) by the calculation section 43, the control section 44 determines that clogging is due to something other than scale, and displays a message for instructing the user to check the filter 22 on the sub operation panel 6 and the main operation panel 7.

When it is determined that there is a correlation between the measured value A and the change-over-time prediction axis 45 by the calculation section 43, the control section 44 determines that clogging is due to scale, and executes a first measure relating to removal of scale, in this case, the scale removal program. For example, a measured value Ay in FIG. 3 is on the change-over-time prediction axis 45 (or, the measured value Ay is within the change-over-time prediction zone 46), and therefore, the calculation section 43 determines that there is a correlation between the measured value Ay and the change-over-time prediction axis 45 (or the change-over-time prediction zone 46). When it is determined that there is a correlation between the measured value Ay and the change-over-time prediction axis 45 (or the change-over-time prediction zone 46) by the calculation section 43, the control section 44 determines that clogging is due to scale, and executes the scale removal program.

When the scale removal program is executed, the calculation section 43 resets the change-over-time prediction axis 45 (or the change-over-time prediction zone 46), and measures a precipitation state of scale over again from the beginning. That is to say, the calculation section 43 measures over again from the measured value A1 in FIG. 3, and calculates the new change-over-time prediction axis 45.

Further, when the pump 30 and the flow rate sensor 31 are replaced in maintenance or the like, with a new pump and a new pressure sensor, numeral values are likely to deviate significantly from the measured values which are measured and stored in the storage section 42 so far. That is to say, the measured value A is unlikely to have a correlation with the change-over-time prediction axis 45. Therefore, when information of performing maintenance such as replacement of the pump 30 and the flow rate sensor 31 is recognized, the calculation section 43 also resets the change-over-time prediction axis 45, and measures the precipitation state of scale over again from the beginning. Note that if exchange is from the old pump 30 to a new pump, the flow rate in the conduit becomes high, and therefore, the calculation section 43 may perform correction of causing the change-over-time prediction axis 45 to slide to an upper side, or inclining a gradient of the change-over-time prediction axis 45 to the upper side without resetting the change-over-time prediction axis 45.

In the scale removal program which is executed when clogging due to scale is detected, the disinfecting solution which is stored in the disinfecting solution tank 33 is discharged, and the inside of the disinfecting solution tank 33 is rinsed with water, after which, the citric acid aqueous solution obtained by predetermined citric acid being dissolved in water is charged into the disinfecting solution tank 33. Thereafter, the citric acid aqueous solution is transferred to the cleaning and disinfecting tank 9 with use of the pump 34 from the disinfecting solution tank 33, and is circulated for a fixed time period with the pumps 25 and 30 so that the citric acid aqueous solution contacts and wets a space surrounded by the circulation conduits 21, 23 and 24, the top cover 3 and the cleaning and disinfecting tank 9.

After the citric acid aqueous solution contacts and wets the space surrounded by the circulation conduits 21, 23 and 24, the top cover 3 and the cleaning and disinfecting tank 9 once, driving of the pumps 25 and 30 may be stopped, and left for a fixed time period. After a lapse of the fixed time period, the citric acid solution is recovered into the disinfecting solution tank 33, or is discharged outside the apparatus main body 2. Thereafter, the inside of the apparatus main body 2 is rinsed with water, and the scale removal program is ended. Note that the aqueous solution for use in the scale removal program is not limited to a citric acid aqueous solution, and can be an acid aqueous solution such as a hydrochloric acid aqueous solution.

Here, a concentration of the citric acid aqueous solution which is used in the scale removal program will be described. FIG. 4 is a diagram for explaining a relation between the concentration of the citric acid aqueous solution and a scale removal result.

As shown in FIG. 4, in a case of a scale component being a calcium carbonate, when a mass percent concentration (hereinafter, simply described as a concentration) of the citric acid aqueous solution is 0.99%, scale is not dissolved, and when the concentration of the citric acid aqueous solution is 4.76%, scale partially remains. When the concentration of the citric acid aqueous solution is 9.09% to 33.3%, scale is completely dissolved.

Further, in a case of the scale component being a tricalcium phosphate, when the concentration of the citric acid aqueous solution is 0.99% and 4.76%, scale is not dissolved, and when the concentration of the citric acid aqueous solution is 33.3%, scale partially remains. When the concentration of the citric acid aqueous solution is 9.09% to 28.6%, scale is completely dissolved.

As above, when the concentration of the citric acid aqueous solution is in a range of 9.09% to 28.6%, scale can be completely dissolved without being influenced by the scale component. That is to say, the concentration of the citric acid aqueous solution which is used in the scale removal program is set in the range of 9.09% to 28.6%, whereby an effect of scale removal can be made the highest.

Further, it is known that by a temperature of the citric acid aqueous solution being increased, a solvent action of scale is enhanced. Therefore, a heater or the like that heats the citric acid aqueous solution is provided in a predetermined position (for example, a back surface of the bottom surface 10t of the tank main body 10) of the endoscope reprocessing apparatus 1. With use of the heater or the like, the citric acid aqueous solution may be heated in a range that does not deteriorate component members of the endoscope reprocessing apparatus 1, for example, in a range of 20° C. to 40° C., and may be circulated into the endoscope reprocessing apparatus 1. By the configuration as above being adopted, the solvent action of scale can be enhanced.

Next, an operation of the endoscope reprocessing apparatus 1 that is configured as above will be described.

Figure 5:
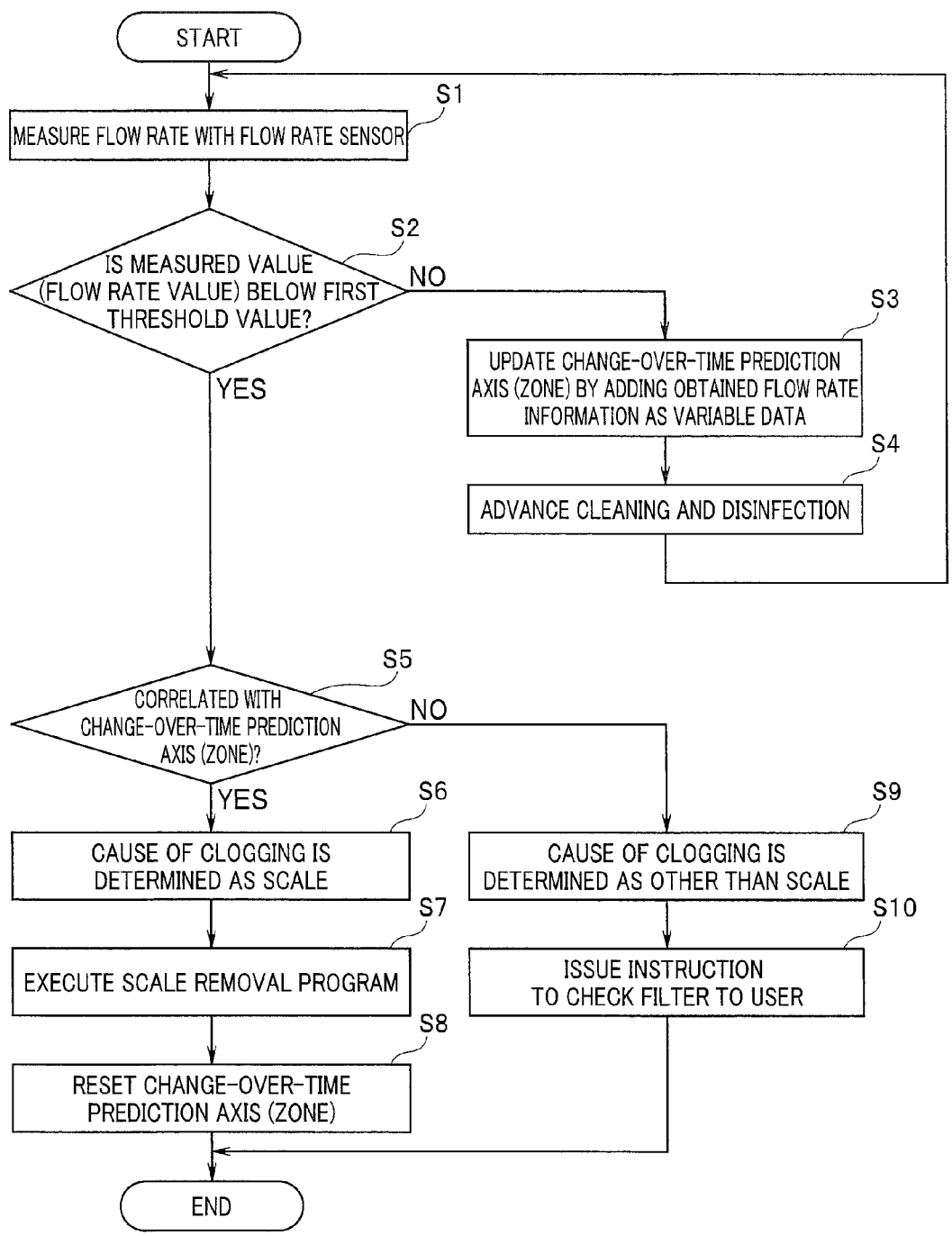
FIG. 5 is a flowchart for explaining scale detection processes of an endoscope reprocessing apparatus 1 according to the first embodiment.

FIG. 5 is a flowchart for explaining scale detection processes of the endoscope reprocessing apparatus 1 according to the first embodiment.

First, the flow rate is measured by the flow rate sensor 31 (step S1), and it is determined whether or not the measured value (the flow rate value) is below the first threshold value (step S2). When it is determined that the measured value (the flow rate value) is not below the first threshold value, the result is NO, the obtained flow rate information is added as variable data, and the change-over-time prediction axis 45 (or the change-over-time prediction zone 46) is updated (step S3). Thereafter, cleaning and disinfecting are advanced (step S4), the flow returns to step S1, and similar processes are repeated.

When it is determined that the measured value (the flow rate value) is below the first threshold value in step S2, the result is YES, and it is determined whether or not the measured value (the flow rate value) has a correlation with the change-over-time prediction axis 45 (or the change-over-time prediction zone 46) (step S5). When it is determined that the measured value (the flow rate value) has a correlation with the change-over-time prediction axis 45 (or the change-over-time prediction zone 46), the result is YES, the cause of clogging is determined to be scale (step S6), and the scale removal program is executed (step S7). Finally, the change-over-time prediction axis (zone) is reset (step S8), and the process is ended.

When it is determined that the measured value (the flow rate value) does not have a correlation with the change-over-time prediction axis (zone), the result is NO, and the cause of clogging is determined to be something other than scale (step S9), an instruction to check the filter 22 is issued to the user (step S10), and the process is ended.

From the above processes, the endoscope reprocessing apparatus 1 determines whether the cause of clogging of the circulation conduits 21 and 24 lies in scale, or lies in something other than scale, and removal means suitable for the cause of clogging, that is, execution of the scale removal program and instruction to check the filter 22 can be performed.

Therefore, according to the endoscope reprocessing apparatus of the present embodiment, the cause of clogging of the apparatus internal conduit is identified, and the removal means suitable for the cause of the clogging can be taken.

(Modification 1)

Next, modification 1 of the first embodiment will be described.

The endoscope reprocessing apparatus 1 of the first embodiment executes the scale removal program when the endoscope reprocessing apparatus 1 determines that clogging by scale has occurred. In relation to this, the endoscope reprocessing apparatus 1 of modification 1 notifies user that clogging by scale has occurred, and causes the user to select whether or not to execute the scale removal program immediately, when the endoscope reprocessing apparatus 1 determines that clogging by scale has occurred.

That is to say, when it is determined that there is a correlation between the measured value A and the change-over-time prediction axis 45 (or the change-over-time prediction zone 46) by the calculation section 43, the control section 44 determines that clogging by scale has occurred, and displays a message saying that clogging by scale has occurred, on the sub operation panel 6 or the main operation panel 7 to notify the user of the occurrence of the clogging. Note that notification to the user is not limited to display of the message by the main operation panel 7 or the like, but, for example, a sound may be generated from a speaker or the like not illustrated, or an LED or the like not illustrated may be lit to notify the user. The sub operation panel 6, the main operation panel 7, the speaker, and the LED configure a notification section.

When the user immediately executes the scale removal program, the user executes the scale removal program by using a scale removal program execution switch that is displayed on the main operation panel 7. For example, when the user executes the scale removal program after cleaning and disinfecting of the endoscopes 51 and 52 are ended, that is, when the user does not execute the scale removal program immediately, the user executes the scale removal program by using the scale removal program execution switch which is displayed on the main operation panel 7, after cleaning and disinfecting of the endoscopes 51 and 52 are ended.

Next, an operation of the endoscope reprocessing apparatus 1 according to modification 1 will be described.

Figure 6:
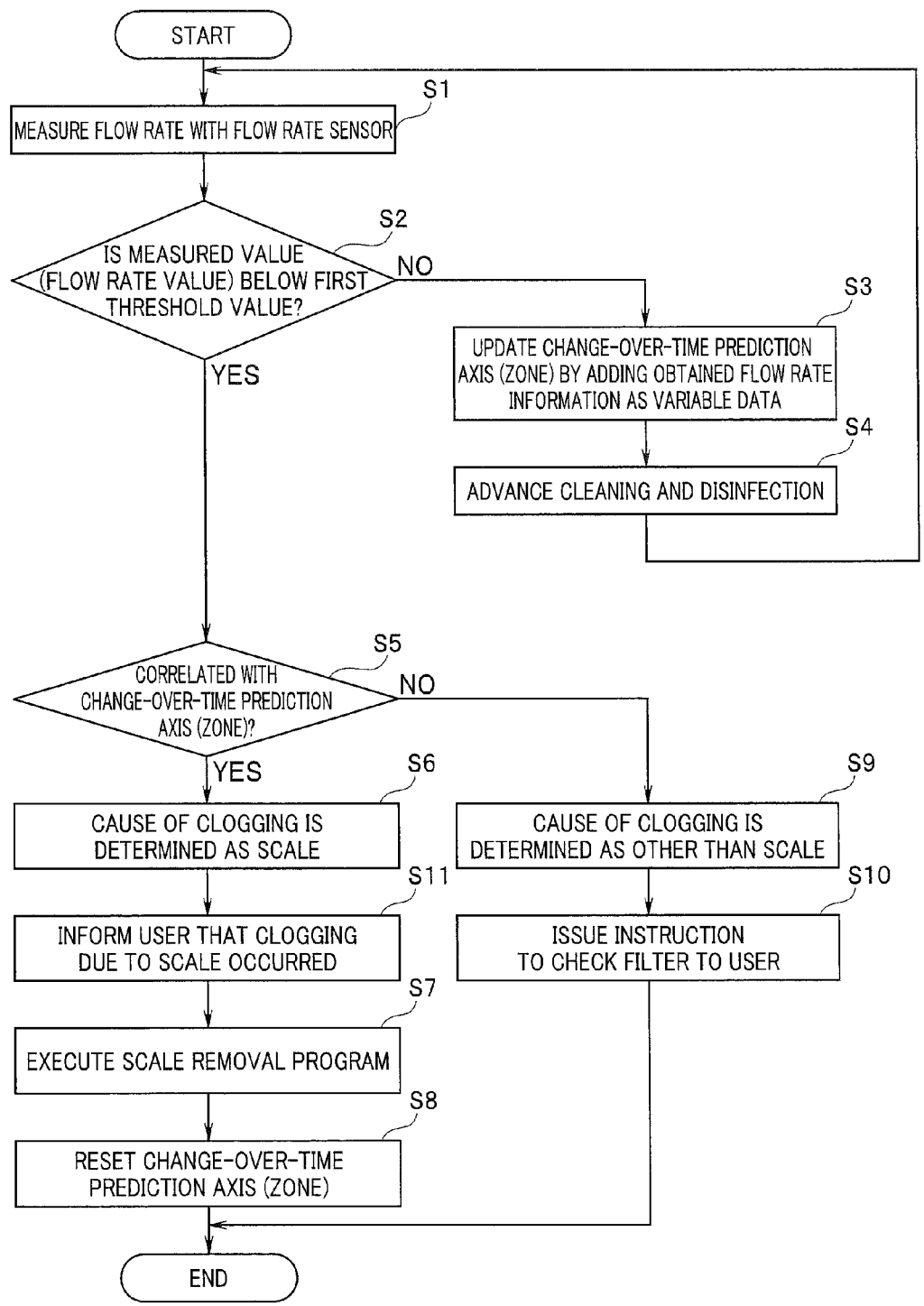
FIG. 6 is a flowchart for explaining scale detection processes of the endoscope reprocessing apparatus 1 according to modification 1.

FIG. 6 is a flowchart for explaining scale detection processes of the endoscope reprocessing apparatus 1 according to modification 1. Note that in FIG. 6, processes similar to the processes in FIG. 5 are assigned with the same reference signs and explanation thereof will be omitted.

When the cause of clogging is determined to be scale in the process in step S6, the user is notified that clogging by scale has occurred (step S11). Thereafter, when the scale removal program by the user is executed in the process in step S7, the change-over-time prediction axis 45 (the change-over-time prediction zone 46) is reset in the process in step S8, and the process is ended. The other processes are similar to the processes in FIG. 5.

By the above processes, the user can execute the scale removal program at an arbitrary timing.

(Modification 2)

Next, modification 2 of the first embodiment will be described.

For example, immediately after use of the endoscope reprocessing apparatus 1 is started, immediately after the scale removal program is executed and the change-over-time prediction axis 45 is reset or the like, a state in which the change-over-time prediction axis 45 (or the change-over-time prediction zone 46) is not calculated is brought about. Immediately after use of the endoscope reprocessing apparatus 1 is started, or the change-over-time prediction axis 45 (or the change-over-time prediction zone 46) is reset or the like, a possibility of clogging due to scale occurring is low. Therefore, the endoscope reprocessing apparatus 1 of modification 2 determines that clogging is due to something other than scale when the change-over-time prediction axis 45 (or the change-over-time prediction zone 46) is not calculated when it is determined that the measured value A is below the first threshold value.

That is to say, when it is determined that the measured value A is below the first threshold value by the calculation section 43, the control section 44 determines whether or not the change-over-time prediction axis 45 (or the change-over-time prediction zone 46) is calculated. Subsequently, when the control section 44 determines that the change-over-time prediction axis 45 (or the change-over-time prediction zone 46) is calculated, it is determined whether or not the measured value A has a correlation with the change-over-time prediction axis 45 (or the change-over-time prediction zone 46), and the control section 44 determines whether clogging is due to scale, or clogging is due to something other than scale. When the control section 44 determines that the change-over-time prediction axis 45 (or the change-over-time prediction zone 46) is not calculated, the control section 44 determines that clogging is due to something other than scale.

Next, an operation of the endoscope reprocessing apparatus 1 according to modification 2 will be described.

Figure 7:
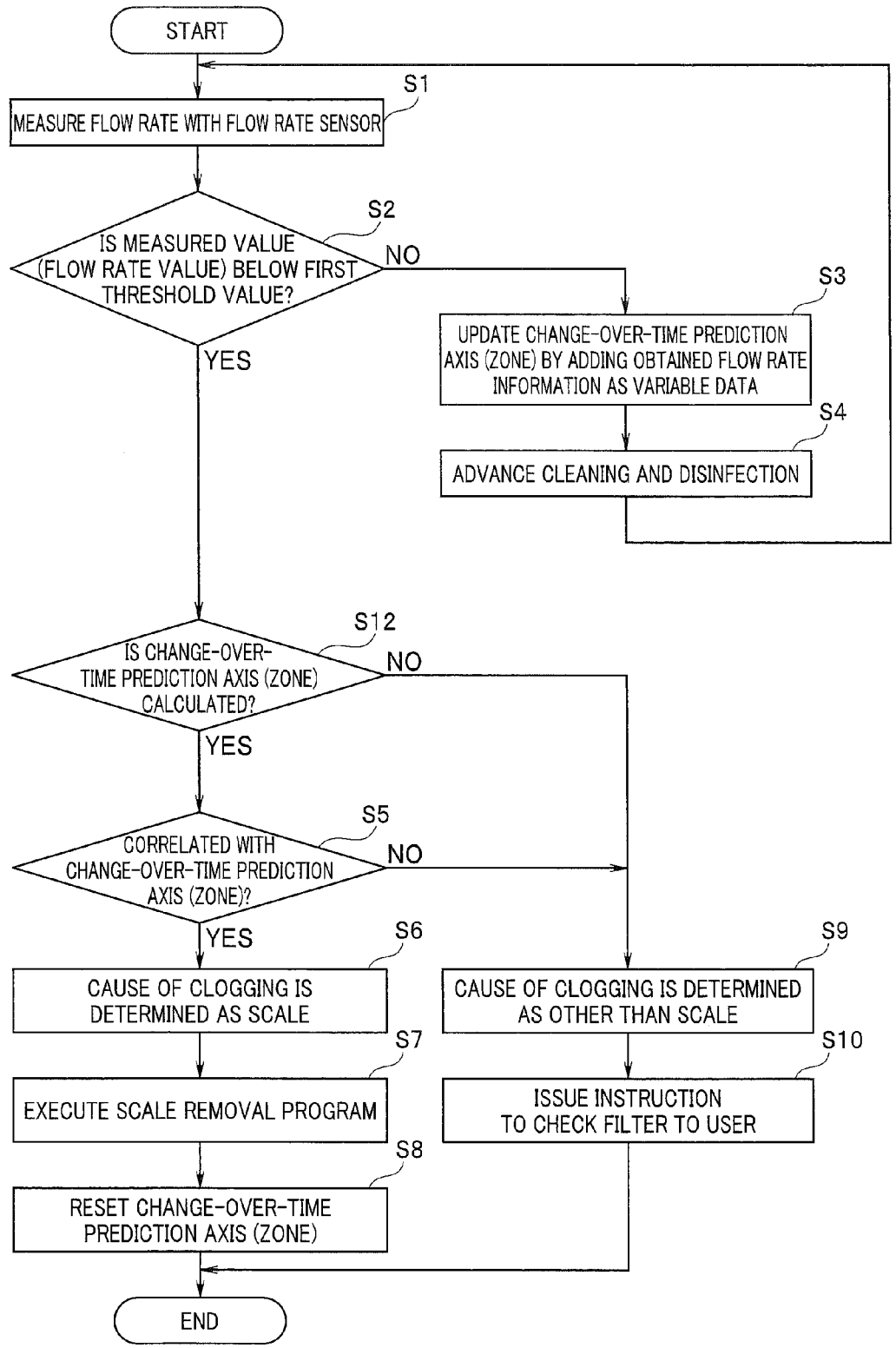
FIG. 7 is a flowchart for explaining scale detection processes of the endoscope reprocessing apparatus 1 according to modification 2.

FIG. 7 is a flowchart for explaining scale detection processes of the endoscope reprocessing apparatus 1 according to modification 2. Note that in FIG. 7, processes similar to the processes in FIG. 5 are assigned with the same reference signs and explanation thereof will be omitted.

When it is determined that the measured value (the flow rate value) is below the first threshold value in the process in step S2, it is determined whether or not the change-over-time prediction axis 45 (or the change-over-time prediction zone 46) is calculated (step S12). When it is determined that the change-over-time prediction axis 45 (or the change-over-time prediction zone 46) is calculated, the result is YES, and it is determined whether or not the measured value (the flow rate value) has a correlation with the change-over-time prediction axis 45 (or the change-over-time prediction zone 46) in the process in step S5. The processes in step S5 and the following steps are similar to the processes in FIG. 5.

When it is determined that the change-over-time prediction axis 45 (or the change-over-time prediction zone 46) is not calculated, the result is NO, and it is determined that the cause of clogging lies in something other than scale in the process in step S9. The processes in step S9 and the following steps are similar to the processes in FIG. 5.

By the above processes, it can be determined that the cause of clogging lies in something other than scale when the clogging occurs in the state in which the change-over-time prediction axis 45 (or the change-over-time prediction zone 46) is not calculated (for example, the state in which the scale removal program is executed, and the change-over-time prediction axis 45 (or the change-over-time prediction zone 46) is reset).

Second Embodiment

Next, a second embodiment will be described.

Figure 8:
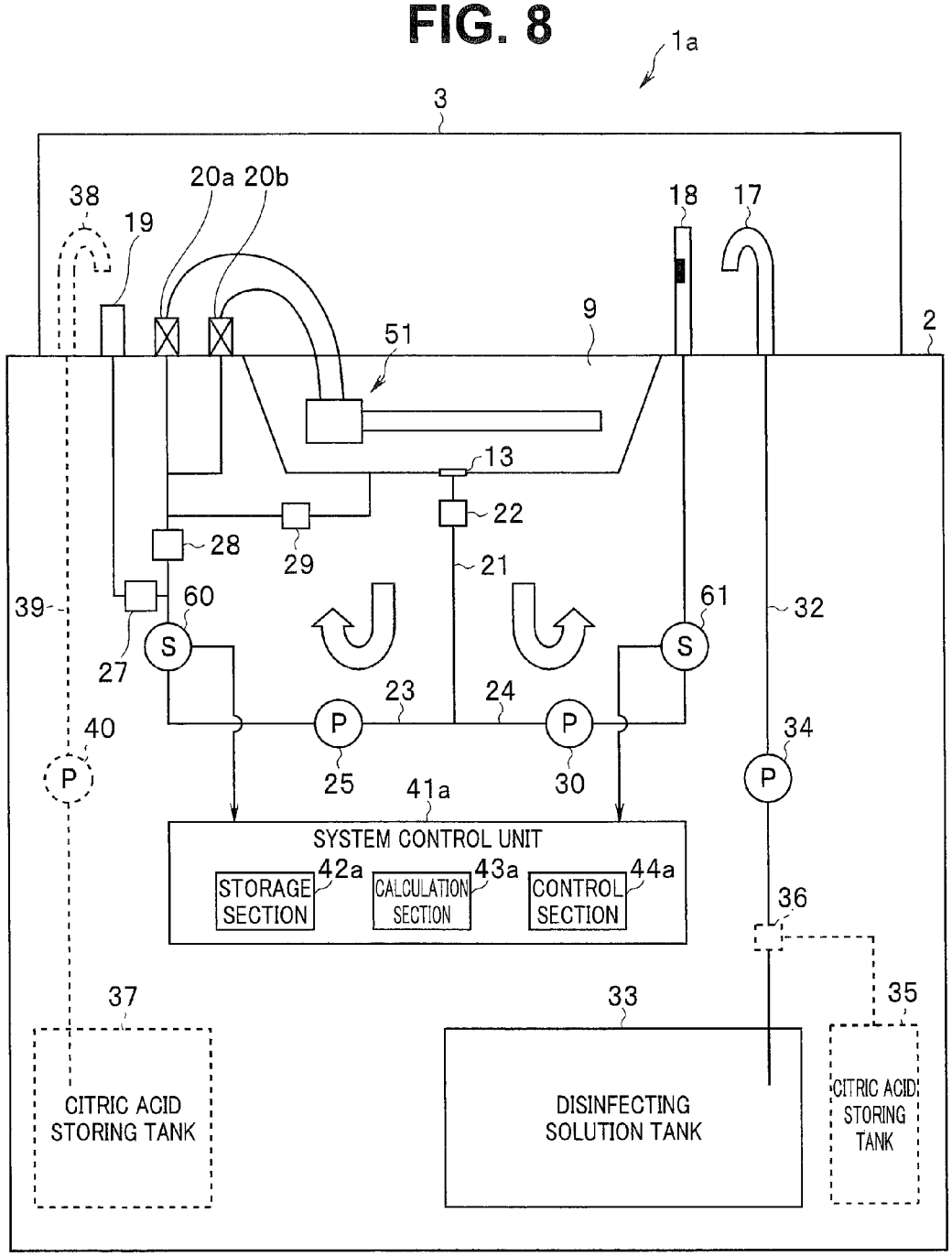
FIG. 8 is a block diagram for explaining an internal configuration of an endoscope reprocessing apparatus according to a second embodiment.

FIG. 8 is a block diagram for explaining an internal configuration of an endoscope reprocessing apparatus according to the second embodiment. Note that in FIG. 8, components that are similar to the components in FIG. 2 are assigned with the same reference signs, and explanation thereof will be omitted.

An endoscope reprocessing apparatus 1a shown in FIG. 8 is configured by using pressure sensors 60 and 61, and a system control unit 41a respectively in place of the flow rate sensors 26 and 31, and the system control unit 41 of the endoscope reprocessing apparatus 1 in FIG. 2. The system control unit 41a is configured by having a storage section 42a, a calculation section 43a and a control section 44a.

The pressure sensors 60 and 61 respectively measure pressures in the circulation conduits 23 and 24, and output measured values (pressure values) that are measured to the system control unit 41a. The pressure sensors 60 and 61 are sensors for detection of scale, and either one of them may be provided as in the first embodiment. Note that in the present embodiment, detection of scale is performed by the pressure sensor 61.

Figure 9A:
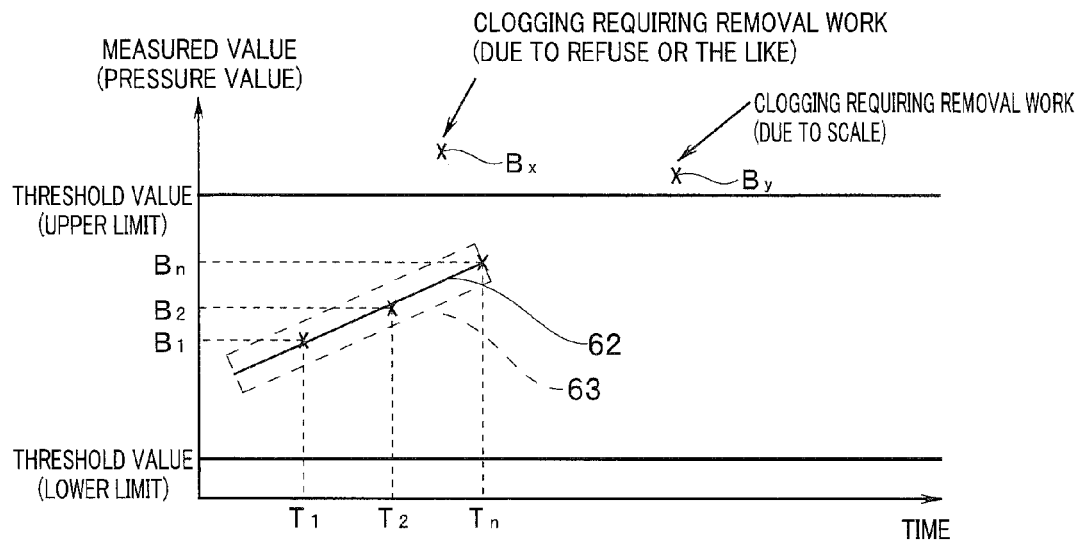
Figure 9B:
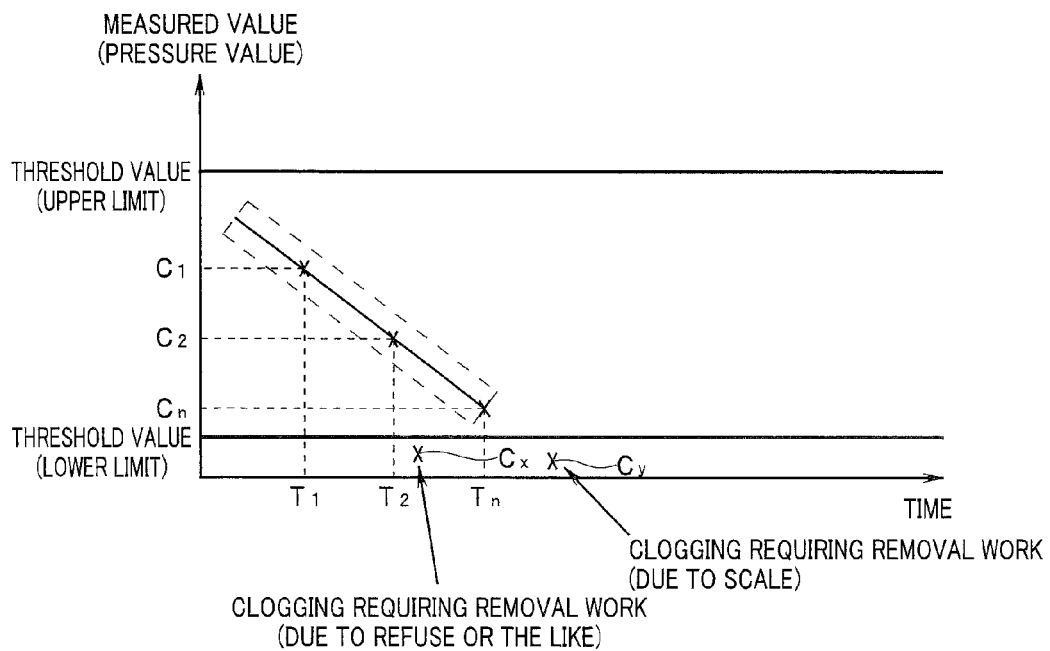

Here, detection of scale by the system control unit 41a will be described with use of FIG. 9A and FIG. 9B. FIG. 9A and FIG. 9B are diagrams for explaining detection of scale by the system control unit 41a.

When cleaning and disinfecting of the endoscopes 51 and 52 are carried out, the pressure sensor 61 measures the pressure in the circulation conduit 24, and outputs a measured value thereof to the system control unit 41a. The calculation section 43a of the system control unit 41a determines whether or not the measured value from the pressure sensor 61 deviates from a threshold value. More specifically, the calculation section 43a determines whether or not the measured value from the pressure sensor 61 is below a first threshold value (a threshold value (a lower limit)), or exceeds a second threshold value (a threshold value (an upper limit)).

For example, when scale precipitates between the pressure sensor 61 and the circulation nozzle 18, the measured value which is measured by the pressure sensor 61 becomes higher as shown in FIG. 9A, as precipitation is advancing. When scale precipitates between the pressure sensor 61 and the circulation port 13, the measured value which is measured by the pressure sensor 61 becomes lower as shown in FIG. 9B, as precipitation is advancing. Therefore, the calculation section 43a determines whether or not the measured value from the pressure sensor 61 is below the first threshold value (the threshold value (the lower limit)), or exceeds the second threshold value (the threshold value (the upper limit)). Note that in the following explanation, detection of scale will be described with use of FIG. 9A.

When the measured value from the pressure sensor 61 is not below the first threshold value, and does not exceed the second threshold value, the calculation section 43a determines that the circulation conduits 21 and 24 do not have clogging, and stores a measured value B thereof in the storage section 42a together with the time point T at a time thereof. As in the first embodiment, a measured value B1 and the time point T1 at a time thereof, a measured value B2 and the time point T2 at a time thereof, . . . , and a measured value Bn and the time point Tn at a time thereof are stored in the storage section 42a.

The calculation section 43a calculates a change-over-time prediction axis 62 from a relation between the measured value B and the time point T which are stored in the storage section 42a. Further, the calculation section 43a may calculate a change-over-time prediction zone 63 which is obtained by a margin given to the change-over-time prediction axis 62.

When the measured value B from the pressure sensor 61 is below the first threshold value, or exceeds the second threshold value, the calculation section 43a determines that the circulation conduits 21 and 24 have clogging. Subsequently, the calculation section 43a determines whether or not there is a correlation between the measured value B and the change-over-time prediction axis 62 (or the change-over-time prediction zone 63).

When it is determined that there is no correlation between the measured value B and the change-over-time prediction axis 62 by the calculation section 43a, the control section 44a determines that clogging is due to something other than scale, and instructs user to check the filter 22. When it is determined that there is a correlation between the measured value B and the change-over-time prediction axis 62 by the calculation section 43a, the control section 44a determines that clogging is due to scale, and executes a scale removal program. Other components are similar to the components of the first embodiment.

Next, an operation of the endoscope reprocessing apparatus 1a which is configured as above will be described.

FIG. 10 is a flowchart for explaining scale detection processes of the endoscope reprocessing apparatus 1a according to the second embodiment. Note that in FIG. 10, processes similar to the processes in FIG. 5 are assigned with the same reference signs, and explanation thereof will be omitted.

First, the pressure is measured by the pressure sensor 61 (step S21), and it is determined whether or not the measured value (the pressure value) is below the first threshold value, or exceeds the second threshold value (step S22). When it is determined that the measured value (the pressure value) is not below the first threshold value, and does not exceed the second threshold value, the result is NO, pressure information that is obtained is added as variable data, and the change-over-time prediction axis 62 (or the change-over-time prediction zone 63) is updated (step S23). Subsequently, in the process in step S4, cleaning and disinfecting are advanced, the flow returns to step S21, and similar processes are repeated.

When it is determined that the measured value (the pressure value) is below the first threshold value, or exceeds the second threshold value in step S22, the result is YES, and it is determined whether or not the measured value (the pressure value) has a correlation with the change-over-time prediction axis 62 (or the change-over-time prediction zone 63) (step S24). When it is determined that the measured value (the pressure value) has a correlation with the change-over-time prediction axis 62 (or the change-over-time prediction zone 63), the result is YES, and it is determined that the cause of clogging lies in scale in step S6, and the scale removal program is executed in step S7. Subsequently, in step S8, the change-over-time prediction axis 62 (or the change-over-time prediction zone 63) is reset, and the process is ended.

When it is determined that the measured value (the pressure value) does not have a correlation with the change-over-time prediction axis 62 (or the change-over-time prediction zone 63), the result is NO, and it is determined that the cause of clogging lies in something other than scale in step S9. Subsequently, in step S10, an instruction to check the filter 22 is issued to the user, and the process is ended.

By the above processes, the endoscope reprocessing apparatus 1a determines whether the cause of clogging in the circulation conduits 21 and 24 lies in scale, or lies in something other than scale, and can take removal means suitable for the cause of clogging.

Therefore, according to the endoscope reprocessing apparatus of the present embodiment, the cause of clogging in the apparatus internal conduits is identified and the removal means suitable for the cause of clogging can be taken similarly to the first embodiment.

Note that modification 1 and modification 2 of the first embodiment may be applied to the endoscope reprocessing apparatus 1a of the present embodiment.

That is to say, when the endoscope reprocessing apparatus 1a determines that clogging by scale has occurred, the endoscope reprocessing apparatus 1a notifies the user that the clogging by scale has occurred, and causes the user to select whether or not to execute the scale removal program immediately.

Further, the endoscope reprocessing apparatus 1a may determine that clogging is due to something other than scale when the change-over-time prediction axis 62 (or the change-over-time prediction zone 63) is not calculated when it is determined that the measured value B is below the first threshold value, or exceeds the second threshold value.

Note that the respective steps in the flowcharts in the present description may be executed by an execution sequence being changed, by a plurality of steps being simultaneously executed, or in a different sequence at each execution, as long as it is not contradictory to the nature thereof.

The present invention is not limited to the aforementioned embodiments, and various modifications, alterations and the like can be made within the range without changing the gist of the present invention.

What is claimed is:

1. An endoscope reprocessing apparatus, comprising:
a fluid supply conduit that supplies a fluid to at least one of a channel or an outer sheath of an endoscope;
a measurement section that measures a flow rate or a pressure of the fluid that flows through the fluid supply conduit;
an information accumulating section that accumulates the flow rate or the pressure which is measured by the measurement section as flow rate or pressure information associated with a measurement timing;
a prediction section that calculates a change-over-time prediction axis of the flow rate or the pressure from the flow rate or pressure information which is accumulated, when a predetermined number or more of pieces of the flow rate or pressure information are accumulated in the information accumulating section;
a threshold value determining section that determines whether the flow rate or pressure information which is measured by the measurement section is in a region in which the fluid supply conduit is determined to be clogged, of a region exceeding a predetermined threshold value and a region below the predetermined threshold value;
a correlation determining section that determines whether or not newest flow rate or pressure information that is measured by the measurement section has a correlation with the change-over-time prediction axis, when the threshold value determining section determines that the flow rate or pressure information is in the region in which the fluid supply conduit is determined to be clogged; and
a control section that performs a first measure relating to removal of scale when the correlation determining section determines that the newest flow rate or pressure information has the correlation, and performs a second measure different from removal of scale when the correlation determining section determines that the newest flow rate or pressure information does not have the correlation.

2. The endoscope reprocessing apparatus according to claim 1, further comprising:
a notification section,
wherein the control section requests a user to introduce a chemical solution that removes scale into the fluid supply conduit by the notification section, as the first measure, and requests the user to check a filter by the notification section, as the second measure.

3. The endoscope reprocessing apparatus according to claim 1, further comprising:
a removal chemical storing section that stores a removal chemical that removes scale,
wherein the control section introduces the removal chemical into the fluid supply conduit from the removal chemical storing section as the first measure.

4. The endoscope reprocessing apparatus according to claim 1,
wherein the prediction section resets the change-over-time prediction axis by setting a number of pieces of the flow rate or pressure information accumulated in the information accumulating section to zero, when the first measure is executed by the control section.

5. The endoscope reprocessing apparatus according to claim 1, further comprising:
a detachably attachable pump that introduces a fluid into the fluid supply conduit,
wherein the prediction section resets the change-over-time prediction axis by setting a number of pieces of the flow rate or pressure information accumulated in the information accumulating section to zero with replacement of the pump, or performs correction of a gradient of the change-over-time prediction axis.

6. The endoscope reprocessing apparatus according to claim 1,
wherein when a number of pieces of the flow rate or pressure information is smaller than the predetermined number, and
the threshold value determining section determines that the flow rate or pressure information is in the region in which the fluid supply conduit is determined to be clogged,
the control section performs the second measure.

7. The endoscope reprocessing apparatus according to claim 1,
wherein the measurement section is a flow rate sensor or a pressure sensor.

* * * * *